United States Patent [19]

Rizkalla

[11] 4,407,726

[45] Oct. 4, 1983

[54] PREPARATION OF CARBOXYLIC ACIDS

[75] Inventor: Nabil Rizkalla, River Vale, N.J.

[73] Assignee: The Halcon SD Group, Inc., New York, N.Y.

[21] Appl. No.: 377,537

[22] Filed: May 12, 1982

Related U.S. Application Data

[60] Division of Ser. No. 267,963, May 28, 1981, Pat. No. 4,372,889, which is a continuation-in-part of Ser. No. 219,786, Dec. 24, 1980.

[51] Int. Cl.$^3$ ............................................. B01J 27/08
[52] U.S. Cl. .................................... 502/161; 502/162; 502/167; 502/169
[58] Field of Search ............... 252/429 R, 430, 431 C, 252/431 N, 431 P, 428

[56] References Cited

U.S. PATENT DOCUMENTS

| | | | |
|---|---|---|---|
| 1,924,768 | 8/1933 | Carpenter | 562/521 |
| 1,957,939 | 5/1934 | Carpenter | 562/521 |
| 3,840,472 | 10/1974 | Colgan et al. | 252/428 X |
| 4,218,340 | 8/1980 | Holmes | 252/429 R |

*Primary Examiner*—Patrick Garvin
*Attorney, Agent, or Firm*—William C. Long; Riggs T. Stewart; Harold N. Wells

[57] ABSTRACT

A carboxylic acid, such as propionic acid, is prepared by carbonylation of an olefin, such as ethylene in the presence of water by the use of a molybdenum-nickel or tungsten-nickel co-catalyst in the presence of a promoter comprising an organo-phosphorus compound or an organo-nitrogen compound wherein the phosphorus and nitrogen are trivalent and in the presence of a halide.

7 Claims, No Drawings

PREPARATION OF CARBOXYLIC ACIDS

REFERENCE TO RELATED APPLICATION

This application is a division of Ser. No. 267,963, filed May 28, 1981 and now U.S. Pat. No. 4,372,889, which is a continuation-in-part of Ser. No. 219,786, filed Dec. 24, 1980.

This invention relates to the preparation of carboxylic acids, more particularly mono-carboxylic acids, and especially lower alkanoic acids, such as propionic acid, by the carbonylation of olefins.

Carboxylic acids have been known as industrial chemicals for many years and large amounts are used in the manufacture of various products. Producing carboxylic acids by the action of carbon monoxide upon olefins (carbonylation) has been described, for example, in Reppe et al. U.S. Pat. No. 2,768,968. However, such prior proposals involving olefin carbonylation reactions have required the use of very high pressures. Olefin carbonylation processes effective at lower pressures have also been proposed. Craddock et al. U.S. Pat. Nos. 3,579,551; 3,579,552 and 3,816,488, for example, describe the carbonylation of olefins in the presence of compounds and complexes of Group VIII noble metals such as iridium and rhodium in the presence of iodide under more moderate pressures than those contemplated by Reppe et al. These lower-pressure carbonylation disclosures, however, require the use of expensive noble metals. More recently, Belgian Pat. No. 860,557 has proposed the preparation of carboxylic acids by carbonylation of alcohols in the presence of a nickel catalyst promoted by a trivalent phosphorus compound and in the presence of an iodide. In this process low pressure carbonylation is made possible without the use of a noble metal. This process is effective but there is room for improvement in terms of yields of the desired acid.

It is accordingly an object of the present invention to provide an improved process for the manufacture of carboxylic acids, especially lower alkanoic acids, such as propionic acid, which requires neither high pressures nor Group VIII noble metals and makes possible the production of carboxylic acids in high yields in short reaction times.

In accordance with the invention, carbonylation of an olefin is carried out by using a molybdenum-nickel or a tungsten-nickel co-catalyst in the presence of a promoter comprising an organo-phosphorus compound or an organo-nitrogen compound wherein the phosphorus and nitrogen are trivalent, and in the presence of a halide, preferably an iodide, a bromide and/or a chloride, especially an iodide and water. The surprising discovery has been made that this co-catalyst in combination with the promoter-halide system of the character indicated makes possible carbonylation of olefins not only at relatively low pressures but with rapid, high yield production of carboxylic acids.

Thus, in accordance with the invention, carbon monoxide is reacted with an olefin such as a lower alkene to produce a carboxylic acid, such as a lower alkanoic acid, the carbonylation taking place in the presence of a halide, e.g., a hydrocarbyl halide, especially a lower alkyl halide, such as ethyl iodide, in the presence of water and in the presence of the co-catalyst and promoter combination which has been identified above. Propionic acid, for example, can be effectively prepared in a representative case by subjecting ethylene to carbonylation.

In like manner, other alkanoic acids, such as butyric acid and valeric acid, can be produced by carbonylating the corresponding lower alkene such as propylene, butene-1, butene-2, the hexenes, the octenes, and the like. Similarly, other alkanoic acids, for example, capric acid, caprylic acid, and lauric acid, and like higher carboxylic acids are produced by carbonylating the corresponding olefin.

The reactant olefin may be any ethylenically unsaturated hydrocarbon having from 2 to about 25 carbon atoms, preferably from 2 to about 15 carbon atoms. The ethylenically unsaturated compound has the following general structure:

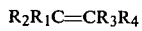

$R_2R_1C\!=\!CR_3R_4$ wherein $R_1$, $R_2$, $R_3$ and $R_4$ are hydrogen or the same or different alkyl, cycloalkyl, aryl, alkaryl, aralkyl or wherein one of said $R_1$ and $R_2$ and one of said $R_3$ and $R_4$ together form a single alkylene group having from 2 to about 8 carbon atoms. $R_1$, $R_2$, $R_3$ and $R_4$ can be branched and can be substituted with substituents which are inert in the reactions of the invention.

Examples of useful ethylenically unsaturated hydrocarbons are ethylene, propylene, butene-1, butene-2, 2-methylbutene-1, cyclobutene, hexene-1, hexene-2, cyclohexene, 3-ethylhexene-1, isobutylene, octene-1, 2-methylhexene-1, ethylcyclohexene, decene-1, cycloheptene, cyclooctene, cyclononene, 3,3-dimethylnonene-1, dodecene-1, undecene-3, 6-propyldecene-1, tetradecene-2, 3-amyldecene-1, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, divinylbenzene, 1-allyl-3-vinylbenzene, etc. Of the olefins referred to above, the alpha hydrocarbon olefins and olefins having 2 to about 10 carbon atoms are preferred, e.g., ethylene, propylene, butene-1, hexene-1, heptene-1, octene-1, and the like, i.e. wherein $R_1$, $R_2$, $R_3$ and $R_4$ are hydrogen or alkyl groups totalling 1–8 carbon atoms, preferably the lower alkenes, i.e. alkenes of 2 to 6 carbon atoms, especially ethylene.

In the most preferred embodiment of the invention carbon monoxide is reacted with ethylene and water in the presence of the co-catalyst-promoter-halide system of the character described above to produce propionic acid in a reaction which may be expressed as follows:

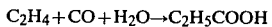

$C_2H_4 + CO + H_2O \rightarrow C_2H_5COOH$

Carbon monoxide is removed in the vapor phase along with unreacted olefin when the olefin is normally gaseous, e.g., ethylene, and, if desired, recycled. Normally-liquid and relatively-volatile components such as alkyl iodide, normally-liquid unreacted olefin and water, and any by-products, present in the final product mixture can be readily removed and separated from each other as be distillation, for recycling, and the net yield of product is substantially exclusively the desired carboxylic acid. In the case of liquid-phase reaction, which is preferred, the organic compounds are easily separated from the metal-containing components, as by distillation. The reaction is suitably carried out in a reaction zone to which the carbon monoxide, the olefin, water, the halide, the co-catalyst and the promoter are fed.

As will be apparent from the foregoing equation, a carbonylation reaction of the character described selective to carboxylic acid requires at least one mole of carbon monoxide and one mole of water per mole (equivalent) of ethylenically unsaturated linkage reacted. Thus, the olefin feedstock is normally charged with equimolar amounts of water, although more water may be used.

In carrying out the process of the invention, a wide range of temperatures, e.g., 25° to 350° C. are suitable but temperatures of 80° to 250° C. are preferably employed and the more preferred temperatures generally lie in the range of 100° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but as previously mentioned, it is a feature of the invention that excessively high perssures, which require special high-pressure equipment, are not necessary. In general, the reaction is effectively carried out by employing a carbon monoxide partial pressure which is preferably at least 15 but less than 2,000 psi, most preferably 15 to 1,000 psi and particularly 30 to 200 psi, although CO partial pressures of 1 to 5,000 or even up to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any organic promoter which may be in the form of a relatively non-volatile complex. The thus recovered co-catalyst as well as promoter, including the iodide component, can then be combined with fresh amounts of olefin, carbon monoxide and water and reacted to produce additional quantities of carboxylic acid.

Although not necessary, the process can be carried out in the presence of a solvent or diluent. The presence of a higher-boiling solvent or diluent, preferably the product acid itself, e.g., propionic acid in the case of ethylene carbonylation will make it possible to employ more moderate total pressures. Alternatively, the solvent or diluent may be any organic solvent which is inert in the environment of the process such as hydrocarbons, e.g., octane, benzene, toluene, xylene and tetralin or carboxylic acids. A carboxylic acid, if used, should preferably correspond to the acid being produced since it is preferred that the solvent employed be indigeous to the system, e.g., propionic acid in the case of ethylene carbonylation, although other carboxylic acids such as acetic acid can also be used. A solvent or diluent, when not the product itself, is suitably selected which has a boiling point sufficiently different from the desired product in the reaction mixture so that it can be readily separated, as will be apparent to persons skilled in the art. Mixtures can be used.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. Hydrogen which may be present as an impurity is not objectionable and even may tend to stabilize the catalyst. Indeed, in order to obtain low CO partial pressures the CO fed may be diluted with hydrogen or any inert gas such as those mentioned above.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Included among the catalyst components listed above are complexes of the metal co-catalyst components with organic promoter ligands derived from the organic promoters hereinafter described.

Particularly preferred are the elemental forms, compounds which are halides, especially iodides, and organic salts, e.g., salts of the monocarboxylic acid corresponding to the acid being produced. It will be understood that the foregoing compounds and complexes are merely illustrative of suitable forms of the several co-catalyst components and are not intended to be limiting.

The specified co-catalyst components employed may contain impurities normally associated with the commercially available metal or metal compounds and need not be purified further.

The organo-phosphorus promoter is preferably a phosphine, e.g. of the formula

wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, imidazole, pyridine, picolines and the like.

Although generally the organic promoter is added separately to the catalyst system, it is also possible to add it as a complex with any of the co-catalyst metals, such as bis(triphenylphosphine) nickel dicarbonyl and tetrakis (triphenyl phosphite) nickel. Both free organic promoters and complexed promoters can also be used. When a complex of the organic promoter and the co-catalyst metal is used, free organic promoter can also be added.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter of reaction mixture, preferably 5 millimols to 500 millimols per liter and most preferably 15 millimols to 150 millimols per liter.

The ratio of nickel to the second co-catalyst component can vary. Typically, it is one mol of the nickel per 0.01 to 100 mols of the second co-catalyst component, preferably the nickel component is used in the amount of 1 mol per 0.1 to 20 mols, most preferably 1 mol per 1 to 10 mols of the second co-catalyst component.

The quantity of organic promoter can also vary widely but typically it is used in the amount of 1 mol per 0.1 to 10 mols of the co-catalyst components, preferably 1 mol per 0.5 to 5 mols, most preferably 1 mol per 1 to 5 mols of the co-catalyst component.

The amount of halide component may also vary widely but, in general, it should be present in an amount of at least 0.1 mol (expressed as elemental halogen) per mol of nickel. Typically, there are used 1 to 100 mols of the halide per mol of nickel, preferably 2 to 50 mols per mol. Ordinarily, more than 200 mols of halide per mol of nickel are not used. It will be understood, however, that the halide component does not have to be added to the system as a hydrocarbyl halide but may be supplied as another organic halide or as the hydrohalide or other inorganic halide, e.g., a salt, such as the alkali metal or other metal salt, or even as elemental halogen.

It will be apparent that the above-described reactions lend themselves readily to continuous operation in which the reactants and catalyst, preferably in combination with the promoter, are continuously supplied to the appropriate reaction zone and the reaction mixture continuously distilled to separate the volatile organic constituents and to provide the desired product or products, e.g., carboxylic acid with the other organic components being recycled and, in the case of liquid-phase reaction, a residual nickel co-catalyst-containing (and promoter-containing) fraction also being recycled.

A particular embodiment of the catalyst comprising the molybdenum-nickel or tungsten-nickel co-catalyst component, the organic promoter component and the halide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1, preferably 5–100:1. The halide is chloride, bromide or iodide, preferably iodide.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 50 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts and all percentages are by weight, unless otherwise indicated.

EXAMPLE 1

In this example, a magnetically-stirred pressure vessel with a glass liner is employed. The reaction vessel is charged with 50 parts water, 20 parts ethyl iodide, 8 parts nickel iodide (NiI$_2$.6H$_2$)), 15 parts molybdenum hexacarbonyl and 150 parts ethyl propionate as solvent. The vessel is swept out with argon and is pressured to 50 p.s.i.g. with hydrogen and up to 400 p.s.i.g. with carbon monoxide. The vessel is then heated to 175° C. with stirring. The pressure is brought up to 800 p.s.i.g. with ethylene. The pressure is maintained at 800 p.s.i.g. by recharging a 1:1 mixture of ethylene and carbon monoxide and the temperature was maintained at 175° C. After 2 hours of reaction time, G.C. analysis of the reaction mixture shows it to contain 48.9 wt. % propionic acid. All of the ethyl propionate charged is recovered in this example and in the following examples.

EXAMPLE 2

A pressure vessel as described in Example 1 is charged with 50 parts water, 20 parts ethyl iodide, 8 parts nickel iodide (NiI$_2$.6H$_2$O), 10 parts molybdenum hexacarbonyl, 20 parts triphenylphosphine, and 150 parts ethyl propionate as solvent. The vessel is swept out with argon and is pressured to 25 p.s.i.g. with hydrogen and up to 150 p.s.i.g. with carbon monoxide. Then the vessel is heated to 175° C. with stirring and the pressure is brought up to 440 p.s.i.g. with ethylene. The pressure is maintained at 440 p.s.i.g. by recharging a 1:1 mixture of ethylene and carbon monoxide and the temperature is maintained at 175° C. After 3 hours of reaction, G.C. analysis of the reaction mixture shows it to contain 56 wt. % propionic acid.

EXAMPLE 3

Example 2 is repeated with the exception that the triphenylphosphine is replaced by an equal amount of tributylphosphine. G.C. analysis of the reaction mixture after 20 minutes of reaction, shows it to contain 42 wt. % propionic acid.

EXAMPLE 4

A pressure vessel as described in Example 1 is charged with 50 parts water, 20 parts iodoethane, 8 parts nickel iodide (NiI$_2$.6H$_2$O), 15 parts molybdenum hexacarbonyl, 10 parts 2-picoline and 150 parts ethyl propionate as solvent. The vessel is swept out with argon and is pressured to 50 p.s.i.g. with hydrogen and up to 350 p.s.i.g. with carbon monoxide. The vessel is heated to 175° C. with stirring and the pressure is brought up to 800 p.s.i.g. using ethylene. The pressure is maintained at 800 p.s.i.g. by recharging a 1:1 mixture of ethylene and carbon monoxide. The temperature is maintained at 175° C. After 3 hours of reaction, G.C. analysis of the reaction mixture shows it to contain 55 wt. % propionic acid.

EXAMPLE 5

Example 4 is repeated except that the 2-picoline is replaced with an equal amount of pyridine. Total conversion of water to propionic acid is achieved in 2 hours.

EXAMPLE 6

A magnetically-stirred pressure vessel with a glass liner is charged with 30 parts water, 250 parts ethyl iodide, 12 parts nickel iodide (NiI$_2$.6H$_2$O), 15 parts molybdenum hexacarbonyl and 30 parts triphenylphosphine. The vessel is swept out with argon and is pressured to 300 p.s.i.g. with ethylene and up to 600 p.s.i.g. with carbon monoxide. The vessel is then heated to 120° C. with stirring and the pressure is brought up to 1,000 p.s.i.g. by means of a 1:1 mixture of ethylene and carbon monoxide. The pressure is maintained at 1,000 p.s.i.g. by recharging a 1:1 mixture of ethylene and carbon monoxide. The temperature is maintained at 120° C. After 15 minutes of reaction, G.C. analysis of the reaction mixture shows it to contain 30 wt. % propionic acid. This represents a 100% conversion of water to propionic acid. No water was found in the effluent.

EXAMPLE 7

Using a reactor as described in Example 6, the vessel is charged with 100 parts water, 150 parts ethyl iodide, 12 parts nickel iodide (NiI$_2$.6H$_2$O), 12 parts molybdenum hexacarbonyl, 20 parts triphenyl phosphine, and 200 parts propionic acid as solvent. The vessel is swept out with argon and is pressured to 50 p.s.i.g. with hydrogen and up to 400 p.s.i.g. with carbon monoxide. The vessel is then heated to 186° C. with stirring. The pressure is brought up to 800 p.s.i.g. by means of ethylene and the pressure is maintained at 800 p.s.i.g. by recharging a 1:1 mixture of ethylene and carbon monoxide. The temperature is maintained at 186° C. After 2½ hours of reaction, G.C. analysis of the reaction mixture shows it to contain 55.6 wt. % propionic acid. The weight increase of the reaction mixture and the analysis indicate that the effluent contains 369.7 parts propionic acid.

EXAMPLE 8

A reactor as described in Example 6 is charged with 30 parts water, 6 parts bis-triphenylphosphine nickel dicarbonyl, 6 parts molybdenum hexacarbonyl, 15 parts triphenylphosphine, 10 parts hydrochloric acid, and 200 parts o-xylene as solvent. The vessel is swept out with argon and is pressured to 100 p.s.i.g. with hydrogen and up to 400 p.s.i.g. with carbon monoxide and is then heated to 190° C. with stirring. The pressure is raised to 1,000 p.s.i.g. using ethylene and the pressure is maintained at 1,000 p.s.i.g. by recharging a 1:1 mixture of ethylene and carbon monoxide. The temperature is maintained at 175° C. After 1 hour of reaction, G.C. analysis of the reaction mixture shows it to contain 13.2 wt. % propionic acid.

EXAMPLE 9

A magnetically-stirred pressure reactor with a glass liner is charged with 200 parts water, 20 parts methyl propionate, 50 parts ethyl iodide, 12 parts nickel iodide, 15 parts molybdenum hexacarbonyl and 30 parts triphenylphosphine. The reactor is swept out with argon and is pressured to 100 p.s.i.g. with hydrogen and up to 500 p.s.i.g. with carbon monoxide. The vessel is then heated to 175° C. with stirring and the pressure is brought to 900 p.s.i.g. by means of a 1:1 mixture of ethylene and carbon monoxide. The pressure is maintained at 900 p.s.i.g. by recharging a 1:1 mixture of ethylene and carbon monoxide and the temperature is maintained at 175° C. After 2½ hours of reaction, G.C. analysis of the reaction mixture shows it to contain 54 wt. % propionic acid. The weight of the reaction effluent is found to be 50% higher than the weight of the charge. This represents a reaction rate of 4.3 mol per liter per hour.

EXAMPLE 10

Example 6 is repeated except that the nickel iodide is replaced with an equivalent amount of nickel tetracarbonyl. Identical results are obtained.

EXAMPLE 11

Example 6 is repeated with the exception that the molybdenum carbonyl is replaced with an equivalent amount of tungsten carbonyl. After 35 minutes of reaction, G.C. analysis shows a total conversion of water to propionic acid.

COMPARATIVE EXAMPLE A

Example 1 is repeated with the exception that no molybdenum is charged. After 3 hours reaction, there is no sign of a pressure drop. G.C. analysis shows no carbonylation of ethylene to propionic acid.

EXAMPLE 12

Using a reactor as described in Example 9, the reactor is charged with 150 parts ethyl propionate as solvent, 50 parts water, 20 parts ethyl bromide, 10 parts molybdenum hexacarbonyl, 8 parts bis-triphenylphosphine nickel dicarbonyl and 20 parts triphenylphosphine. The reactor is pressured to 25 p.s.i.g. with hydrogen and then to 150 p.s.i.g. with carbon monoxide and is heated to 128° C. Ethylene is then introduced to raise the pressure to 480 p.s.i.g. and the pressure is maintained at 480 p.s.i.g. by introducing a 1:1 mixture of ethylene and carbon monoxide. The reaction is carried out for 2 hours at 178° C. G.C. analysis shows that 134.4 parts of propionic acid are formed.

EXAMPLE 13

Example 12 is repeated except that the ethyl bromide is replaced with 20 parts chloroethane and the reactor is pressured to 500 p.s.i.g. with ethylene and the reaction is carried out for 3 hours at 175° C. G.C. analysis shows that 100 parts of propionic acid are made, giving a 33 wt. % propionic acid concentration in the reaction mixture.

What is claimed is:

1. A liquid-phase carbonylation catalyst comprising a molybdenum-nickel or tungsten-nickel co-catalyst component, an organic promoter component and a halide component represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or a hydride; Z is a halide source which is hydrogen halide, halogen, an alkyl halide wherein the alkyl group contains 1 to 20 carbon atoms or an alkali metal halide, and Q is an organo-phosphorus compound or an organo-nitrogen compound wherein the phosphorus and the nitrogen are trivalent, the molar ratio of X to T being 0.1–10:1, the molar ratio of X+T to Q being 0.05–20:1 and the molar ratio of Z to X+T being 1–1,000:1, the halide being chloride, bromide or iodide, said organo-phosphorus compound being a phosphine of the formula

wherein $R^1$, $R^2$ and $R^3$ may be the same or different, and are alkyl, cycloalkyl, aryl or amide groups or halogen atoms, containing 1 to 20 carbon atoms in the case of alkyl and cycloalkyl groups and 6 to 18 carbon atoms in the case of aryl groups, and said organo-nitrogen compound being a tertiary amine, an amide, a hydroxy amine, a keto amine, a di-, tri-, or other polyamine or a nitrogen-containing compound which comprises two or more other functional groups.

2. A catalyst as defined in claim 1, wherein said organo-phosphorus compound is selected from the group consisting of trimethylphosphine, tripropylphosphine, tricyclohexylphosphine, and triphenylphosphine.

3. A catalyst as defined in claim 1, wherein said organo-nitrogen compound is selected from the group consisting of 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, imidazole, pyridine, and picolines.

4. A catalyst as defined in claim 1, wherein said organo-phosphorus compound is selected from the group consisting of trimethylphosphine, tripropylphosphine, tricyclohexylphosphine, and triphenylphosphine, and said organo-nitrogen compound is selected from the group consisting of 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, imidazole, pyridine, and picolines.

5. A catalyst as defined in claim 1, wherein the halide is an iodide.

6. A catalyst as defined in claim 1, wherein X is molybdenum.

7. A catalyst as defined in claim 1, wherein Q is a phosphine.

* * * * *

UNITED STATES PATENT AND TRADEMARK OFFICE
CERTIFICATE OF CORRECTION

PATENT NO. : 4,407,726
DATED : Oct. 4, 1983
INVENTOR(S) : Nabil Rizkalla

It is certified that error appears in the above-identified patent and that said Letters Patent is hereby corrected as shown below:

On the title page;

Change title to --CATALYST COMPRISING NICKEL AND MOLYBDENUM OR TUNGSTEN--

Signed and Sealed this

Sixteenth Day of July 1985

[SEAL]

Attest:

DONALD J. QUIGG

Attesting Officer

Acting Commissioner of Patents and Trademarks